United States Patent
Lev et al.

(10) Patent No.: US 11,800,984 B2
(45) Date of Patent: Oct. 31, 2023

(54) SENSOR FUSION FOR MEASUREMENT OF PHYSIOLOGICAL PARAMETERS

(71) Applicant: NEC Corporation Of America, Herzlia (IL)

(72) Inventors: Tsvi Lev, Tel-Aviv (IL); Yaacov Hoch, Ramat-Gan (IL)

(73) Assignee: NEC Corporation Of America, Herzlia (IL)

( * ) Notice: Subject to any disclaimer, the term of this patent is extended or adjusted under 35 U.S.C. 154(b) by 7 days.

(21) Appl. No.: 17/575,673

(22) Filed: Jan. 14, 2022

(65) Prior Publication Data

US 2022/0133157 A1 May 5, 2022

Related U.S. Application Data

(63) Continuation of application No. 17/007,000, filed on Aug. 31, 2020, now Pat. No. 11,357,411, which is a
(Continued)

(51) Int. Cl.
*A61B 5/02* (2006.01)
*A61B 5/0205* (2006.01)
(Continued)

(52) U.S. Cl.
CPC ........ *A61B 5/02055* (2013.01); *A61B 5/0022* (2013.01); *A61B 5/015* (2013.01);
(Continued)

(58) Field of Classification Search
CPC .... A61B 5/02055; A61B 5/0022; A61B 5/015
See application file for complete search history.

(56) References Cited

U.S. PATENT DOCUMENTS

| 10,846,857 B1 | 11/2020 | Graves et al. |
| 2003/0135097 A1* | 7/2003 | Wiederhold ........... A61B 5/117 600/509 |

(Continued)

OTHER PUBLICATIONS

Notice of Allowance dated Mar. 9, 2022 from US Patent and Trademark Office Re. U.S. Appl. No. 16/923,132. (35 pages).
(Continued)

*Primary Examiner* — Hugh Maupin

(57) ABSTRACT

There is provided a system for measuring a physiological parameter of a person indicative of physiological pathology, comprising: a plurality of remote non-contact sensors, each of a different type of sensing modality, at least one hardware processor executing a code for: simultaneously receiving over a time interval, from each of the plurality of remote non-contact sensors monitoring a person, a respective dataset, extracting, from each respective dataset, a respective sub-physiological parameter of a plurality of sub-physiological parameters, analyzing a combination of the plurality of sub-physiological parameters, and computing a physiological parameter indicative of physiological pathology according to the analysis, wherein an accuracy of the physiological parameter computed from the combination is higher than an accuracy of the physiological parameter independently computed using any one of the plurality of sub-physiological parameters.

18 Claims, 7 Drawing Sheets

Related U.S. Application Data continuation-in-part of application No. 16/923,132, filed on Jul. 8, 2020, now Pat. No. 11,361,445.

(51) Int. Cl.
*A61B 5/00* (2006.01)
*A61B 5/18* (2006.01)
*A61B 5/01* (2006.01)

(52) U.S. Cl.
CPC .............. *A61B 5/18* (2013.01); *A61B 5/4836* (2013.01); *A61B 5/6803* (2013.01); *A61B 5/7267* (2013.01); *A61B 2562/0271* (2013.01)

(56) References Cited

U.S. PATENT DOCUMENTS

| | | | | |
|---|---|---|---|---|
| 2009/0326383 | A1* | 12/2009 | Barnes | A61B 5/417 850/1 |
| 2013/0215928 | A1 | 8/2013 | Bellifemine | |
| 2014/0378810 | A1* | 12/2014 | Davis | G06F 16/245 600/407 |
| 2015/0106020 | A1 | 4/2015 | Chung et al. | |
| 2015/0112606 | A1 | 4/2015 | He et al. | |
| 2017/0017852 | A1 | 1/2017 | Su et al. | |
| 2019/0216333 | A1 | 7/2019 | Lai et al. | |
| 2019/0236342 | A1 | 8/2019 | Madden et al. | |
| 2020/0342245 | A1 | 10/2020 | Lubin et al. | |
| 2021/0236053 | A1* | 8/2021 | Narayan | A61B 5/363 |
| 2021/0302238 | A1 | 9/2021 | Beall | |
| 2021/0304537 | A1 | 9/2021 | Reed et al. | |
| 2021/0334581 | A1 | 10/2021 | Gandara et al. | |
| 2021/0364356 | A1 | 11/2021 | Stewart et al. | |
| 2022/0007950 | A1 | 1/2022 | Lev et al. | |
| 2022/0012894 | A1 | 1/2022 | Lev | |
| 2022/0344060 | A1* | 10/2022 | Kristal | G16H 50/50 |

OTHER PUBLICATIONS

Notice of Allowance dated Mar. 17, 2022 From the US Patent and Trademark Office Re. U.S. Appl. No. 17/007,000. (17 Pages).

Official Action dated Dec. 6, 2021 from US Patent and Trademark Office Re. U.S. Appl. No. 17/007,000. (24 pages).

Official Action dated Nov. 10, 2021 from the US Patent and Trademark Office Re. U.S. Appl. No. 16/923,132. (18 pages).

* cited by examiner

SENSOR FUSION FOR MEASUREMENT OF PHYSIOLOGICAL PARAMETERS

RELATED APPLICATIONS

This application is a Continuation of U.S. patent application Ser. No. 17/007,000 filed on Aug. 31, 2020, which is a Continuation-in-Part (CIP) of U.S. patent application Ser. No. 16/923,132 filed on Jul. 8, 2020, the contents of which are incorporated by reference as if fully set forth herein in their entirety.

FIELD AND BACKGROUND OF THE INVENTION

The present invention, in some embodiments thereof, relates to measurements of physiological parameters and, more specifically, but not exclusively, to systems and methods for computing a physiological parameter indicative of physiological pathology.

During viral outbreaks, such as COVID-19 and/or flu, people are screened to determine likelihood of the person suffering from respirator pathology attributed to the viral outbreak. Sensors are used to help screen people for detecting likelihood of respiratory pathology. For example, a thermometer placed underneath a tongue of a person is used to take the temperature of a person to detect if the person has high temperature indicative fever likely linked to respiratory pathology, or normal range temperature. In another example, a pulse oximeter placed on a finger of a person measures heart rate and oxygen saturation (SpO2). High heart rate and/or low oxygen saturation are linked to respiratory pathology.

SUMMARY OF THE INVENTION

According to a first aspect, a system for measuring a physiological parameter of a person indicative of physiological pathology, comprises: a plurality of remote non-contact sensors, each of a different type of sensing modality, at least one hardware processor executing a code for: simultaneously receiving over a time interval, from each of the plurality of remote non-contact sensors monitoring a person, a respective dataset, extracting, from each respective dataset, a respective sub-physiological parameter of a plurality of sub-physiological parameters, analyzing a combination of the plurality of sub-physiological parameters, and computing a physiological parameter indicative of physiological pathology according to the analysis, wherein an accuracy of the physiological parameter computed from the combination is higher than an accuracy of the physiological parameter independently computed using any one of the plurality of sub-physiological parameters.

According to a second aspect, a method of measuring a physiological parameter of a person indicative of physiological pathology, comprises: simultaneously receiving over a time interval, a respective dataset from each of a plurality of remote non-contact sensors each of a different type of sensing modality that are monitoring a person, extracting, from each respective dataset, a respective sub-physiological parameter of a plurality of sub-physiological parameters, analyzing a combination of the plurality of sub-physiological parameters, and computing a physiological parameter indicative of physiological pathology according to the analysis, wherein an accuracy of the physiological parameter computed from the combination is higher than an accuracy of the physiological parameter independently computed using any one of the plurality of sub-physiological parameters.

According to a third aspect, a computer program product for measuring a physiological parameter of a person indicative of physiological pathology, comprises: a non-transitory memory having stored thereon a code for executing by at least one hardware processor, comprising instructions for: simultaneously receiving over a time interval, a respective dataset from each of a plurality of remote non-contact sensors each of a different type of sensing modality that are monitoring a person, extracting, from each respective dataset, a respective sub-physiological parameter of a plurality of sub-physiological parameters, analyzing a combination of the plurality of sub-physiological parameters, and computing a physiological parameter indicative of physiological pathology according to the analysis, wherein an accuracy of the physiological parameter computed from the combination is higher than an accuracy of the physiological parameter independently computed using any one of the plurality of sub-physiological parameters.

In a further implementation form of the first, second, and third aspects, further comprising code for: prior to the extracting: detecting errors according to an analysis of a combination of the datasets when time synchronized, correcting and/or removing the detected errors from the datasets, wherein the extracting is performed for each respective dataset for which the detected errors are corrected and/or removed.

In a further implementation form of the first, second, and third aspects, further comprising code for: prior to the extracting: detecting errors according to an analysis of each respective dataset, excluding a certain dataset with detected errors from extraction of at least one certain sub-physiological parameter, wherein the extracting excludes extracting the at least one certain sub-physiological parameter from the excluded certain dataset.

In a further implementation form of the first, second, and third aspects, each sub-physiological parameter denotes a measurement of a different physiological manifestation of the person, and the physiological parameter indicates a diagnosis of likelihood of physiological pathology, wherein none of the sub-physiological parameters when used independently are indicative of the diagnosis of likelihood of physiological pathology.

In a further implementation form of the first, second, and third aspects, the plurality of sub-physiological parameters and corresponding remote non-contract sensors are selected from the group consisting of: (i) temperature computed from an analysis of a thermal images captured by a thermal sensor, (ii) respiratory rate and/or breathing pattern computed from an analysis of data outputted by a sensor selected from the group consisting of: a thermal sensor, a radar sensor, a Doppler sensor, and a short wave infrared sensor (SWIR) sensor, (iii) heart rate and/or heartbeat pattern computed from an analysis of data outputted by a sensor selected from the group consisting of: a radar sensor, a Doppler sensor, a thermal sensor, and a visual light sensor, (iv) oxygen saturation (SpO2) computed from an analysis of data outputted by a sensor selected from the group consisting of: a SWIR sensor, and a visual light sensor, (v) one or more of: nasal congestion, sore throat, hoarse voice, and cough, obtained from an analysis of an acoustic dataset outputted by an acoustic sensor.

In a further implementation form of the first, second, and third aspects, the subject is in a vehicle, and the respective datasets depict the subject in the vehicle captured with a window of the vehicle open.

In a further implementation form of the first, second, and third aspects, further comprising code for generating instructions for admitting the vehicle to a parking area when a value of the physiological pathology is below a threshold.

In a further implementation form of the first, second, and third aspects, further comprising code for analyzing at least one of the respective datasets obtained from at least one of the plurality of remote non-contact sensors for validating that a set of rules is met, and in response to the set of rules being met, performing the extracting, the analyzing the combination, and the computing the physiological parameter, wherein the set of rules includes at least one rule selected from a group consisting of: a subject is in a vehicle, a window of the vehicle is open, a location of the subject and/or vehicle is according to a target location, an engine of the vehicle is turned off, and vibrations of the vehicle are below a threshold.

In a further implementation form of the first, second, and third aspects, further comprising at least one of: (i) automatically generating instructions to a controller that controls an automatic door to open the door for admission of the person when the diagnosis indicates unlikelihood of physiological pathology, and to close the door and/or maintain the door in the closed state to prevent admission of the person when the diagnosis indicates likelihood of physiological pathology, and (ii) administering an effective treatment for treatment of the physiological pathology, the treatment selected from the group consisting of: supplemental oxygen, antibiotics, anti-viral, mechanical ventilation, bronchodilators, and corticosteroids.

In a further implementation form of the first, second, and third aspects, one of the plurality of sub-physiological parameters comprise a breathing pattern, and one of the remote non-contact sensors comprise a thermal sensor capturing a sequence of thermal images depicting an open mouth of the person, and further comprising code for: computing the breathing pattern by analyzing changes in pixel intensity values of pixels corresponding to a mouth cavity of the person in the sequence of thermal images.

In a further implementation form of the first, second, and third aspects, each sub-physiological parameter denotes a different respective measurement originating from a same single physiological manifestation of the person, and the physiological parameter indicative of physiological pathology is a single measurement of the same single physiological manifestation.

In a further implementation form of the first, second, and third aspects, a time interval of the datasets used for computing the physiological parameter is shorter than a time interval of each respective dataset required to compute each respective sub-parameter with an accuracy similar to an accuracy of the physiological parameter.

In a further implementation form of the first, second, and third aspects, the same single physiological manifestation indicative of physiological pathology is selected from the group consisting of: (i) respiratory rate and/or breathing pattern, (ii) heart rate and/or heartbeat pattern, and (iii) blood oxygen saturation (SpO2), and wherein the datasets and corresponding remote non-contract sensors include two or more sensors selected from the group consisting of: (i) thermal images acquired by a thermal sensor, (ii) near infrared (NIR) images acquired by a NIR sensor, (iii) visual light images acquired by a visual light sensor, and a (iv) dataset indicative of chest motion captured by a Doppler sensor and/or radar sensor.

In a further implementation form of the first, second, and third aspects, one of the plurality of sub-physiological parameters comprise a breathing pattern, and one of the remote non-contact sensors comprise a thermal sensor capturing a sequence of thermal images depicting a face of the person, and further comprising code for: computing the breathing pattern by analyzing changes in pixel intensity values of pixels corresponding to nostrils and/or face mask of the person in the sequence of thermal images.

In a further implementation form of the first, second, and third aspects, further comprising code for segmenting the nostrils and/or mask of the person in the sequence of thermal images by identifying regions of changes in pixel intensity values, the change in pixel intensity values varies by an amount corresponding to a temperature change range, and a rate of change of the pixel intensity values corresponding to a candidate breathing rate range.

In a further implementation form of the first, second, and third aspects, the breathing pattern is computed as a breathing rate based on a time interval from maximal to maximal pixel intensity values of pixels corresponding to the nostril and/or face mask of the sequence of thermal images.

In a further implementation form of the first, second, and third aspects, analyzing changes in pixel intensity values comprises analyzing an average intensity value of intensity values of pixels depicting the face mask and/or nostrils.

In a further implementation form of the first, second, and third aspects, the change in pixel intensity values of pixels corresponding to the face mask excludes pixels of the face mask corresponding to a nose of the person.

In a further implementation form of the first, second, and third aspects, the breathing pattern is computed by analyzing changes in pixel intensity values of pixels corresponding to a region on a face of the person under a nose of the person in the sequence of thermal images.

In a further implementation form of the first, second, and third aspects, further comprising code for analyzing the sequence of thermal images to identify a plurality of facial features and/or mask features indicative of regions of each thermal image depicting parts of a face of the person, wherein the breathing pattern is computed by analyzing changes in pixel intensity values of pixels corresponding to nostrils and/or face mask of the person according to the identified plurality of facial features and/or mask features.

In a further implementation form of the first, second, and third aspects, a first of the plurality of remote non-contact sensors comprises a thermal and/or visual sensor capturing a sequence of thermal and/or visual images depicting a chest and/or head of the person, a second of the plurality of remote non-contact sensors comprises a Doppler and/or radar sensor, and further comprising code for: analyzing at least one thermal and/or visual image to identify a target location of the chest and/or head of the person, and generating instructions for adjustment of a steering mechanism for adjusting an orientation of the Doppler and/or radar sensor for capturing the dataset from the identified target location, wherein a first sub-physiological parameter is extracted from a first dataset acquired by the thermal and/or visual sensor, and a second sub-physiological parameter is extracted from a second dataset acquired by the Doppler and/or radar sensor.

In a further implementation form of the first, second, and third aspects, further comprising code for: analyzing a first dataset acquired by a first remote non-contact sensor to obtain tracked locations on a plurality of fixed points on a head of the person, receiving a second dataset depicting the head of the person acquired by a second remote non-contact sensor, and correcting the second dataset using the fixed points of the first dataset, for tracking the plurality of fixed points on the head of the person depicted in the second dataset.

In a further implementation form of the first, second, and third aspects, the extracting and the analyzing and the computing the physiological parameter comprises obtaining an outcome of a classifier trained on a training dataset including, for each of a plurality of subjects, a respective dataset acquired by each of the plurality of remote non-contact sensors, and an associated label of the physiological parameter indicative of physiological pathology.

In a further implementation form of the first, second, and third aspects, at least one of the plurality of sub-physiological parameters comprises a demographic parameter, and wherein the analyzing the combination of the plurality of sub-physiological is according to a baseline defining physiological pathology according to the demographic parameter.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1:
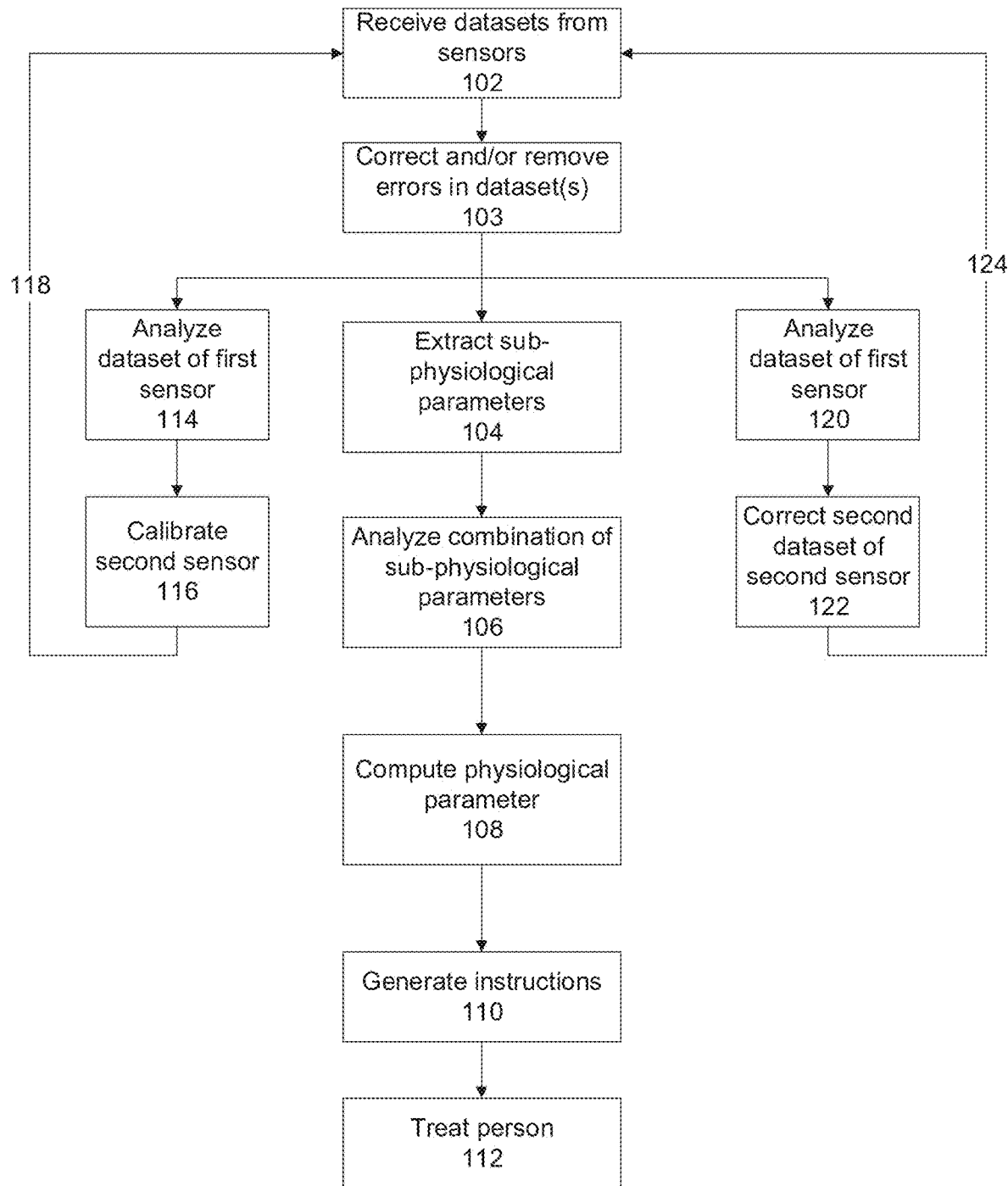
FIG. 1 is a flowchart of a method for measuring a physiological parameter of a person indicative of physiological pathology, in accordance with some embodiments of the present invention.

The present invention, in some embodiments thereof, relates to measurements of physiological parameters and, more specifically, but not exclusively, to systems and methods for computing a physiological parameter indicative of physiological pathology.

An aspect of some embodiments of the present invention relates to a system, an apparatus, a method, and/or code instructions (i.e., stored on a memory and executable by one or more hardware processors) for measuring a physiological parameter of a person, optionally the physiological parameter being indicative of physiological pathology, for example, respiratory, cardiovascular, skin pathology, mental state pathology (e.g., delirium, dementia, drug induced), and the like. The respiratory pathology is optionally caused by a viral infection, for example, COVID-19, flu, and the like. Multiple datasets are simultaneously received from respective remote, non-contact sensors, each of a different type of sensor modality, for example, thermal images, visible light images, ultrasound, laser speckle imaging, Lidar, and radar. A respective sub-physiological parameter may be extracted from each respective dataset. A combination of the sub-physiological parameters is analyzed. Alternatively or additionally, a combination of the datasets is analyzed, for example, a correlation between the two datasets. The combination of datasets may be analyzed without necessarily extracting the sub-physiological parameter from each dataset. A physiological parameter indicative of physiological pathology is computed according to the analysis. The accuracy of the physiological parameter computed from the combination of sub-physiological parameters and/or combination of datasets is higher than an accuracy the physiological parameter computed independently for each one of the sub-physiological parameters, and/or computed for a subset of sub-physiological parameters that is smaller than the full set of sub-physiological parameters from all sensors. In response to the computed physiological parameter, instructions may be automatically generated, for example, for execution by a controller for automatically opening a door to enable entry into an enclosure for people that are unlikely infected by a viral disease. It is also possible that detection of potential pathology will lead to further screening by additional methods. For example, a person suspected of respiratory pathology may be sent for x-ray imaging, and/or a person suspected of cardiovascular pathology may be sent for ECG. In another example, the subject may be located within a vehicle, with the datasets of the subject captured while the subject is inside the vehicle, optionally with the windows down. Entry of the vehicle into a parking area (e.g., parking lot, garage) and/or further driving (e.g., crossing a border, entering a city, entering a toll highway, crossing a bridge, boarding a ferry) may be denied when the subject is determined to have the physiological pathology such as according to a set of rules such as the value of the physiological parameter being above a threshold (e.g., by automatically generating instructions for execution by a control to activate a mechanism to close a gate and/or keep the gate closed). Entry of the vehicle may be permitted when the subject is determined not to have physiological pathology such as according to the set of rules such as the value of the physiological parameter being below the threshold (e.g., by automatically generating instructions for execution by a control to activate a mechanism to open a gate).

Optionally, in a first implementation, each respective sensor represents a different physiological manifestation of the person. Different sub-physiological parameters are computed for each respective dataset acquired by each respective sensor, for example, temperature is computed from thermal images outputted by a thermal sensor, and heart rate is computed from a radar sensor. The physiological parameter indicative of physiological pathology, for example, likelihood of being infected with the viral disease, is computed from the combination of different sub-physiological parameters indicative of different respective physiological manifestations.

Alternatively, in a second implementation, the respective dataset acquired by each respective sensor represents a similar (e.g., same) single physiological manifestation of the person. The same single sub-physiological parameter may be computed for each respective dataset acquired by each respective sensor, for example, respiratory rate is computed from a combination of thermal images captured by a thermal sensor, and chest motion captured by a radar sensor. The physiological parameter indicative of physiological pathology, for example, likelihood of being infected with the viral disease, is computed from the combination of similar/same sub-physiological parameters indicative of similar/same respective physiological manifestations.

In some embodiments of the first and/or second implantation, the physiological parameter cannot be computed independently from any other (or subset smaller than the full set) of the respective sub-physiological parameters. The physiological parameter is computed from the combination of the full set of sub-physiological parameters from the full set of datasets of sensor. An accuracy of the physiological parameter computed independently from any one of the respective sub-physiological parameters is lower than a threshold, and/or lower than the physiological parameter computed from the combination of sub-physiological parameters. The accuracy of the physiological parameter computed from the combination of sub-physiological parameters may be above the threshold. The combination of datasets from the multiple sensors increases the accuracy of computing the physiological parameter, and/or enables computing the physiological parameter, in comparison to using the datasets independently and/or using fewer datasets than used in the combination. Optionally, when the physiological parameter indicates a likelihood of a diagnosis of the physiological pathology, for example, likelihood of respiratory pathology such as due to being infected with the viral infection such as COVID-19, none of the sub-physiological parameters when used independently are indicative of likelihood of the diagnosis. The combination of the sub-physiological parameters increases the accuracy and/or enables the computation of the physiological parameter.

At least some implementations of the systems, methods, apparatus, and/or code instructions described herein address the technical problem of rapid and/or accurate screening of people for likelihood of physiological pathology. At least some implementations of the systems, methods, apparatus, and/or code instructions described herein improve the technology of rapid and/or accurate screening of people for likelihood of physiological pathology.

Likelihood of physiological pathology may be detected, for example, using contact sensors that provide highly accurate measurements. Since such contact sensors are highly accurate, only a single sensor type is used to acquire the data. For example, a thermometer placed under the tongue of the person that measures temperature, a pulse oximeter sensor placed on a finger of a person that measures heart rate and/or oxygen saturation (SpO2), and/or wearable contact sensors that measure respiratory rate and/or heart rate. There are several technical problems with such accurate contact sensors. One example of a problem is that such contact sensors are irrelevant for rapid screening of people for physiological pathology, due to lack of time to acquire a proper reading, infection and safety issues from reuse of contact sensors for different people, and privacy issues in forcing people to undergo contact based measurements. For example, checking people suffering from a viral disease, such as COVID-19, during an outbreak. Non-contact temperature sensors are routinely used, for example, to screen people entering a shopping mall, boarding flights, entering other enclosures, and/or cars entering parking areas and/or other driving zones. Such non-contact temperature sensors are inaccurate in measuring temperature. Moreover, COVID-19 presents differently in different people, such that a person with no apparent fever may be infected with COVID-19, make some measurements such as temperature inaccurate in detecting people infected with COVID-19.

There are other technical problems with other sensors used for detecting likelihood of physiological pathology. First, as discussed above, some physiological pathologies, for example respiratory pathology such as COVID-19, may present with a different constellation of symptoms in different people. So screening for such respiratory pathologies such as COVID-19 using a single sensor is inherently accurate in that the single sensor will miss those that are infected but not presenting the symptom sensed by the sensor, such as fever. Second, non-contact sensors tend to be less accurate than contact sensors, for example, due to errors in the remotely acquired data, interference from other sources (e.g., affected by strong electromagnetic (EM) signals generated from an interfering source), and/or situations where such sensors do not work well (e.g., person wearing thick and/or dark jacket distorts temperature data of thermal images of the body underneath the jacket). Third, the time to acquire sufficient data by a certain sensor for an accurate measurement may be long. For example, a video of thermal images may require greater than 30 seconds, or more than 1 minute or longer, in order to have sufficient data to estimate a certain physiological parameter. Such delay may be unacceptable, for example, for screening passengers loading onto a plane, or entering a movie theater, in particular when the lineup is long.

At least some implementations of the systems, methods, apparatus, and/or code instructions described herein provide solutions to one or more of the above mentioned technical problems, by using multiple sensors, optionally non-contact, optionally of different modalities, that capture respective dataset, optionally simultaneously. For example, a thermal sensor (e.g., IR camera) captures thermal images at the same time as a radar sensor captures motion displacement data. The outputs of the sensors are fused, i.e., a combination of the datasets, and/or a combination of sub-physiological parameters extracted from respective datasets, is analyze to compute a physiological parameter indicative of physiological pathology. The fusion of the outputs of the sensors, where each sensor outputs a different dataset based on a different modality, and a different sub-physiological parameter is extracted from each dataset, enables detection of likelihood of physiological pathology in patients where the constellation of symptoms differs between patients. For example, respiratory rate is estimated from thermal images, temperature is estimated from the thermal images, heart rate is estimated from the Doppler and/or radar sensor, and oxygen saturation is estimated from a SWIR and/or RGB sensor. The fusion of data from the multiple sensors may improve likelihood and/or accuracy of detecting COVID-19 and/or other physiological pathologies that present with different combinations of symptoms in different people. Alternatively or additionally, in another implementation, fusion of the outputs of the sensors, where each sensor outputs a different dataset based on a different modality, and the same sub-physiological parameter is extracted from each dataset, enables improved accuracy of measurement of a single physiological parameter, which may indicate likelihood of the physiological pathology. For example, respiratory rate is measured by fusion of datasets acquired by a radar sensor, and a thermal sensor. The respiratory rate measured by the fusion of the datasets is more accurate than the respiratory rate measured only by the radar sensor, and/or more accurate than the respiratory rate measured only by the thermal sensor. Moreover, the time required for the radar sensor and the thermal sensor to obtain enough data for accurate measurement of the respiratory rate, when the data of the two sensors is fused, may be sufficiently shorted that the amount of time required for only one of the two sensors to obtain enough data for accurate measurement of the respiratory rate. Further, in some cases, data acquired by only one of the sensors may be insufficient for computing the physiological parameter (e.g., respiratory rate), at all. In such a case, fusion of data from two or more sensors is required to compute the physiological parameter. It is noted that the two implementations may be combined, for example, using two or more different sensors to measure two or more different sub-physiological parameters, and using at least two of the sensors to obtain a more accurate measure of one of the sub-physiological parameters.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 2:
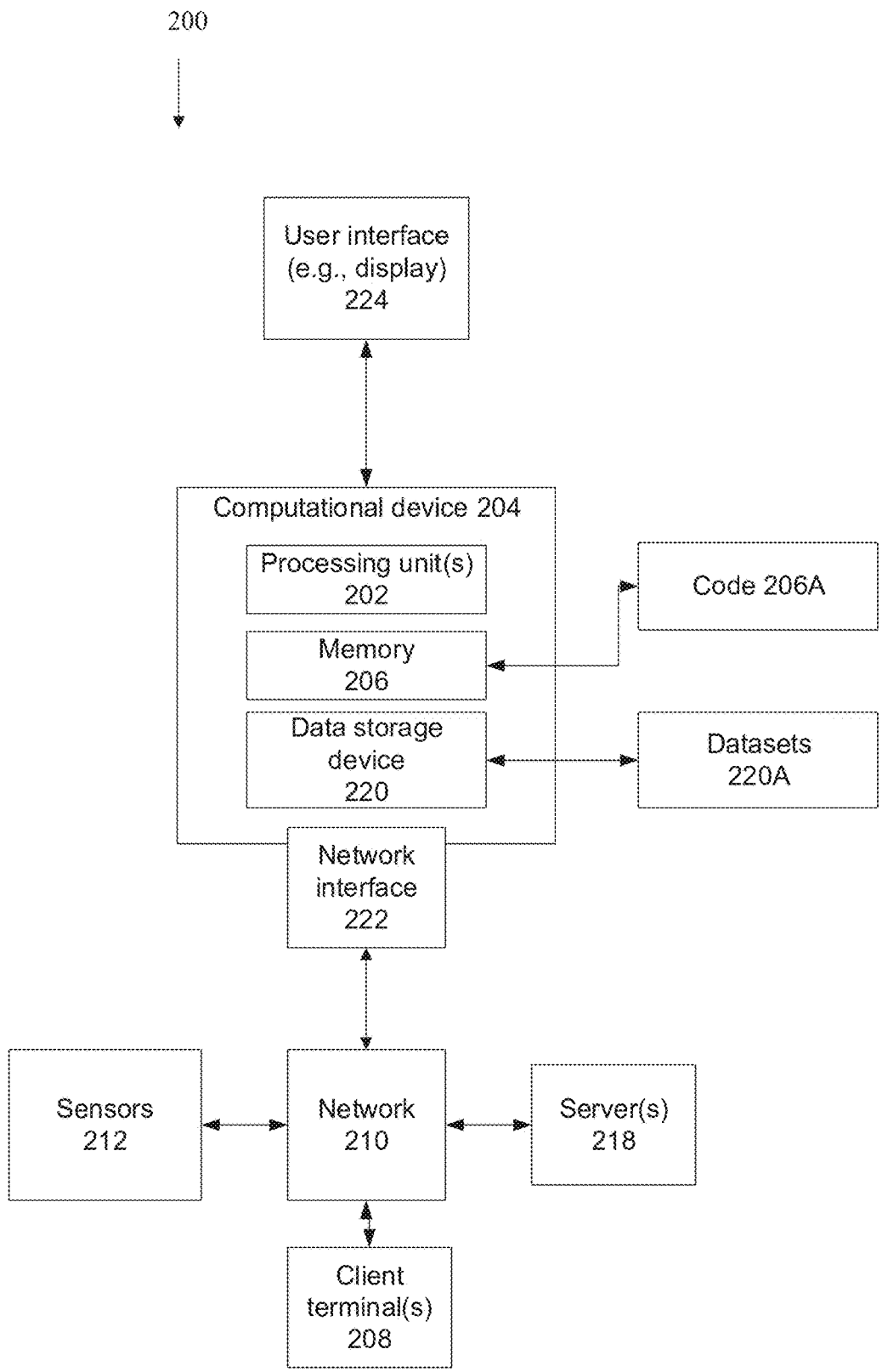
FIG. 2 is a block diagram of components of a system for measuring a physiological parameter of a person indicative of physiological pathology, in accordance with some embodiments of the present invention.

Reference is now made to FIG. 1, which is a flowchart of a method for measuring a physiological parameter of a person indicative of physiological pathology, in accordance with some embodiments of the present invention. Reference is also made to FIG. 2, which is a block diagram of components of a system 200 for measuring a physiological parameter of a person indicative of physiological pathology, in accordance with some embodiments of the present invention. System 200 may implement the features of the method described with reference to FIG. 1, by one or more hardware processors 202 of a computing device 204 executing code instructions stored in a memory (also referred to as a program store) 206.

Computing device 204 may be implemented as, for example, a client terminal, a server, a virtual machine, a virtual server, a computing cloud, a mobile device, a desktop computer, a thin client, a Smartphone, a Tablet computer, a laptop computer, a wearable computer, glasses computer, and a watch computer.

Multiple architectures of system 200 based on computing device 204 may be implemented. In an exemplary implementation, computing device 204 storing code 206A may be implemented as one or more servers (e.g., network server, web server, a computing cloud, a virtual server) that provides services (e.g., one or more of the acts described with reference to FIG. 1) to one or more servers 218 and/or client terminals 208 over a network 210, for example, providing software as a service (SaaS) to the servers 218 and/or client terminal(s) 208, providing software services accessible using a software interface (e.g., application programming interface (API), software development kit (SDK)), providing an application for local download to the servers 218 and/or client terminal(s) 208, and/or providing functions using a remote access session to the servers 218 and/or client terminal(s) 208, such as through a web browser and/or viewing application. For example, users use client terminals 208 to access computing device 204 to provide the datasets acquired by the multiple sensors, and/or view and/or receive the physiological parameter indicative of physiological pathology. For example, using an installed application and/or by using a web browser to connect to computing device 204, and/or communicating data with computing device 204 using a software interface (application programming interface (API) and/or software development kit (SDK). In another example, computing device 204 is a standalone system, for example, a laptop connected to sensors 212 and running locally stored code 206A.

Computing device 204 receives datasets acquired by multiple sensors 212, optionally non-contact remote sensors. Examples of sensors 212 include: a thermal sensor capturing thermal images of radiation that correlates with temperature (e.g., in the long-infrared (IR) range of the electromagnetic spectrum (e.g., about 9000-14000 nanometers)), InGaAs sensors, FPA sensors, short-wave infrared (SWIR) sensors, near infrared (NIR) sensors, standard visible light sensors (e.g., CCD and/or CMOS sensors, such as red, green, blue (RGB) sensors), radar sensors, ultrasound sensors, laser speckle imaging, Lidar, and biometric sensors. Sensor 212 may include acoustic sensors. Sensor 212 may transmit acquired datasets to computing device 204, for example, via a direct connected (e.g., local bus and/or cable connection and/or short range wireless connection), and/or via a network 210 and a network interface 222 of computing device 204 (e.g., where sensors are connected via internet of things (IoT) technology and/or are located remotely from the computing device).

Network interface 222 may be implemented as, for example, a wire connection (e.g., physical port), a wireless connection (e.g., antenna), a network interface card, a wireless interface to connect to a wireless network, a physical interface for connecting to a cable for network connectivity, and/or virtual interfaces (e.g., software interface, API, SDK, virtual network connection, a virtual interface implemented in software, network communication software providing higher layers of network connectivity).

Memory 206 stores code instructions executable by hardware processor(s) 202. Exemplary memories 206 include a random access memory (RAM), read-only memory (ROM), a storage device, non-volatile memory, magnetic media, semiconductor memory devices, hard drive, removable storage, and optical media (e.g., DVD, CD-ROM). For example, memory 206 may code 206A that execute one or more acts of the method described with reference to FIG. 1.

Computing device 204 may include data storage device 220 for storing data, for example, datasets(s) 220A acquired by sensors 212, as described herein. Data storage device 220 may be implemented as, for example, a memory, a local hard-drive, a removable storage unit, an optical disk, a storage device, a virtual memory and/or as a remote server 218 and/or computing cloud (e.g., accessed over network 210). It is noted that dataset(s) 220A may be stored in data storage device 220, for example, with executing portions loaded into memory 206 for execution by processor(s) 202.

Computing device 204 and/or client terminal(s) 208 include and/or are in communication with one or more physical user interfaces 224 that include a mechanism for entering data and/or viewing data, for example, a touchscreen display used to indicate a new person for analysis, and/or for presenting the computed physiological parameter Exemplary user interfaces 224 include, for example, one or more of, a touchscreen, a display, a keyboard, a mouse, and voice activated software using speakers and microphone.

Server(s) 218 may receive instructions generated by computing device 204. For example, server 218 may be implemented as a controller of an automated door that is automatically opened based on the instructions in response to the physiological parameter indicative of non-likelihood of physiological pathology, and is automatically closed and/or locked based on the instructions in response to the physiological parameter indicative of likelihood of physiological pathology.

Referring now back to FIG. 1, at 102, respective datasets are received from each one of multiple remote, non-contact sensors monitoring a person. Each respective dataset may be the output of the respective sensor, for example, a video including multiple frames, sequentially acquired individual still frames, and respective values indicative of other measurements made by the respective sensor. The respective dataset may be the raw output of the respective sensor, and/or output that has been processed to obtain a value. For example, raw signals that correspond to displacement of the chest of the person, or a value indicating the amount of displacement of the chest.

The datasets may include an acoustic dataset obtained from an acoustic recording.

The respective datasets are simultaneously received from the multiple sensors that simultaneously acquire and/or output the respective dataset.

The respective datasets are simultaneously received over a time interval. In the first implementation where the respective dataset acquired by each respective sensor represents a different physiological manifestation of the person, the time interval may be long enough to enable sufficient amount of data in each respective dataset to compute the respective physiological manifestation, for example, at an accuracy above a threshold. In the second implementation where the respective dataset acquired by each respective sensor represents a similar (e.g., same) physiological manifestation of the person, the time interval may be short enough so that the data in each respective dataset is insufficient to compute the physiological manifestation at an accuracy above a threshold. The time interval may be shorter than a time interval of each respective dataset required to compute each respective sub-parameter with an accuracy similar to an accuracy of the physiological parameter.

The time interval may be too short for using only one sensor, or fewer than the total number of sensors, to accurate compute the physiological manifestation at an accuracy above the threshold. As described herein, in at least some implementations, using the combination of datasets from the multiple sensors, even when obtained over a time interval that is too short for using each dataset independently, provides for computing the physiological manifestation at the accuracy above the threshold.

At 103, the respective datasets may be analyzed for errors. Optionally, the combination of time synchronized dataset are analyzed for errors. The detected errors may be corrected and/or the errors may be eliminated in the respective datasets. Alternatively or additionally, the dataset with identified errors is excluded from extraction of certain sub-physiological parameters. The dataset with identified errors may be used to extract other sub-physiological parameters which may be unaffected by the error. The correction and/or removal of the errors and/or exclusion of the dataset may improve reliability and/or accuracy of the subsequently extracted sub-physiological parameter(s) and/or computation of the physiological parameter.

The errors may be detected, for example, by correlating synchronized portions of the datasets to each other, and identifying non-correlated portion of the datasets, for example, when a correlation value falls to below a threshold, and/or when a correlation value for the correlated datasets falls more than a predefined amount of a certain portion of the datasets. In another example the errors may be detected by computing features of the datasets and comparing the features to predefined non-error and/or error values (e.g., using a set of rules), for example, maximum value, standard deviation, expected patterns, and the like. Features may be extracted for each dataset alone, and/or for a combination of the datasets (e.g., sum of two datasets, different between two datasets, peaks/troughs in both dataset) In another example, the errors may be detected by feeding the datasets (each alone, and/or in a combination) into an error classifier trained on datasets obtained from other people using similar sensors, and labelled with an indication of error or non-error.

Some examples of removing and/or correcting errors are provided.

In one example, selective elimination/removal of some of the sensor datasets is performed when such datasets are deemed irrelevant. For example, when the person wears a thick sweater/coat, a first sensor (e.g., used to provide the dataset from which heart rate and/or respiratory rate sub-physiological parameters are extracted) aimed at the chest may generate irrelevant dataset from which the heart rate and/or respiratory rate cannot be extracted (e.g., especially for heart rate) while another sensor aimed at the carotid artery at the throat or at the face may still output a dataset from which heart rate may be extracted. In such a case, the first dataset of the first sensor may be removed from further processing. The removal may eliminate errors due to the processing of the irrelevant first dataset. In another example the person may have a thick beard, a scarf, and the chest area. In such a case, the second dataset is removed, and the first dataset is used.

In another example, human motion (intentional and/or unintentional) during the measurement may affect some sensors datasets more than others. For example, motion may affect the reliability of computing the respiratory rate sub-physiological parameter more than that of computing the heartbeat/temperature/oximetry sub-physiological parameter. The dataset may be analyzed to detect motion (e.g., analyzes images outputted by RGB/IR image sensors or other sensors to detect excessive motion of the person). The dataset with motion may be excluded from computation of the respiration parameter sub-physiological parameter.

In yet another example, electronic instrumentation may affect radar sensors. The dataset outputted by the radar sensor may be analyzed to determine whether the dataset is affected by electronic instrumentation. The errors may be corrected and/or removed.

In yet another example, the time synchronized datasets (e.g., time series) are analyzed as a combination. For example, the air outflow from the nostrils/mouth, which may be computed from a first dataset of a first sensor, is expected to correlate with chest contraction/distance increase from a second dataset of a second sensor that is time synchronized with the first sensor. Errors may be detected when correlation is poor, for example, below a threshold. Such errors may be removed from further processing. When correlation is good, for example, above a threshold, the time synchronized datasets represent high quality and/or accurate measurements. The validity and/or quality of the data may be enhanced significantly by intelligently combining the datasets in the time-series form. It is noted that the second dataset of the sensor may not necessarily correlate with the time synchronized first dataset of the first sensor.

In yet another example, a combination of the time synchronized datasets may help detect errors, and/or improve extraction of some sub-physiological parameters. For some sensors, there may significant 'crosstalk' between the various datasets outputted by the sensors. For example, breathing and heartbeat extracted sub-physiological parameters of the person may correspond in some areas and in some sensors to the same physical measurement (e.g., distance of chest/throat) obtained from the same dataset. When the Breathing frequency sub-physiological parameter may be considered omega_1 (e.g., $\frac{1}{15}$ of hertz (Hz)) and the heart-rate sub-physiological parameter may be considered omega_2 (e.g., 1 Hz), the following frequencies with similar amplitude may be detected: omega_2+omega_1, omega_2−omega_1, omega_2. Having a separate estimate from another sensor of either omega_1 or omega_2 may help isolate the values of omega_1 and omega_2.

In yet another example, at least one of the respective datasets obtained from at least one of the remote non-contact sensors is analyzed for validating that a set of rules is met. In such implementation, the analysis for errors may be, for example, to determine when the set of rules is not met (i.e., error) or when the set of rules is met (i.e., no error). Alternatively or additionally, other data obtained from other sensors is analyzed to determine whether the set of rules is met. When the set of rules is met, the remaining features of the method described with reference to FIG. 1 may be implemented, for example, one or features described with reference to 104-124 of FIG. 1. When the set of rules is not met, an indication may be generated, for example, a message (e.g., text message presented on a display, an audio recording played over speakers, a video played on the display) indicating what the problem is and/or how to fix the problem in order to meet the set of rules. The set of rules may be, for example, to evaluate whether the data captured of a subject in a vehicle is reliable for processing. Exemplary set of rules include one or more of: the subject is in the vehicle, the window of the vehicle is open, a location of the subject and/or vehicle is according to a target location (e.g., subject is in the front seat, vehicle positioned in front of sensor to enable sensor to capture data), an engine of the vehicle is turned off, and vibrations of the vehicle are below a threshold. Examples of instructions that are generated when the set of rules is not met may include one or more of: subject should sit still in vehicle and look towards the sensor(s), open window, move car forward/reverse relative to sensor(s), turn engine off, vehicle vibrating too much—turn off engine and/or subject to exit vehicle.

At 104, a respective sub-physiological parameter is extracted from each respective dataset of each respective sensor.

According to the first implementation, different respective sub-physiological parameters are extracted from respective datasets. Examples of sub-physiological parameters and corresponding remote non-contract sensors from which respective datasets used to compute the corresponding respective sub-physiological parameter include:

Temperature computed from an analysis of thermal images captured by a thermal sensor capturing thermal images.

Respiratory rate and/or breathing pattern computed from an analysis of data outputted by a sensor, for example, a thermal sensor, a radar sensor, a Doppler sensor, and a short wave infrared sensor (SWIR) sensor.

Heart rate and/or heartbeat pattern computed from an analysis of data outputted by a sensor, for example, a radar sensor, a Doppler sensor, a thermal sensor, and a visual light sensor.

Oxygen saturation (SpO2) computed from an analysis of data outputted by a sensor, for example, a SWIR sensor, and a visual light sensor.

Nasal congestion, sore throat, hoarse voice, cough, and the like, obtained from an analysis of an acoustic dataset outputted by an acoustic sensor.

According to the second implementation, the same and/or similar sub-physiological parameter is extracted from each respective dataset. Examples of sub-physiological parameters representing the same and/or similar single physiological manifestation indicative of physiological pathology include: respiratory rate and/or breathing pattern, heart rate and/or heartbeat pattern, and blood oxygen saturation (SpO2). Examples of different datasets and corresponding remote non-contract sensors from which the same and/or similar sub-physiological parameter is computed include thermal images acquired by a thermal sensor, near infrared (NIR) images acquired by a NIR sensor, visual light images acquired by a visual light sensor, and a dataset indicative of chest motion captured by a Doppler sensor and/or radar sensor.

Optionally, one of the sub-physiological parameters is a breathing pattern indicative of breathing of the person. In some embodiments, one of the remote non-contact sensors may be a thermal sensor capturing a sequence of thermal images depicting a face of the person. The breathing pattern may be computed by analyzing changes in pixel intensity values of pixels, which are indicative of heating and cooling, corresponding to nostrils and/or mouth cavity (i.e., of an open mouth) and/or face mask of the person in the sequence of thermal images. The change in pixel intensity values corresponding to the nostril and/or mouth cavity and/or face mask may be performed by analyzing the average of pixel intensity values of pixels depicting the face mask and/or nostrils and/or mouth cavity, for example, in segmented regions of the mask and/or face. The change in pixel intensity values of pixels corresponding to the face mask may exclude pixels of the face mask corresponding to the nose of the person. The heating and/or cooling pattern of the nose may be different than the rest of the mask, and not necessarily correlated with breathing pattern, since the nose may heat up and remain at a substantially constant temperature thereafter. The heating and/or cooling of the face mask that excludes the nose may correlate with breathing patterns, indicative of cooling of the mask during inhalation and heating of the mask during exhalation. In some embodiments, the nostrils and/or mouth cavity and/or mask of the person in the sequence of thermal images may be segmented, for example, by identifying regions of changes in pixel intensity values. The nostrils and/or mouth cavity aren't visible in the image and/or the nostrils and/or mouth cavity cannot be accurately detected (e.g., above a threshold) in the image, for example, when the person is properly wearing a mask covering the nose and mouth, and/or when the person is looking downwards. In such a case, the breathing pattern may be computed by analyzing changes in pixel intensity values of pixels corresponding to a region on the face of the person under the nose of the person, for example, the lips, the philtrum, and nasolabial sulcus.

Optionally, one or more of the sub-physiological parameters may be demographic parameters of the person, for example, age, gender, weight, and/or height. The demographic parameters may be obtained by an analysis of a single images or one or more images captured by sensors, for example, infrared and/or RBG image sensors. The demographic parameters may be obtained, for example, by feeding the respective image into a demographic classifier trained on a training dataset of images of different people captured by the sensor, labelled with an indication of the demographic parameter of the person depicted in the image. Other approaches include, for example, performing physical measurements of the person from the images, such as counting the number of pixels the person spans in the image and based on the calibration of distance per pixel, the height and/or weight may be estimated (e.g., using a weight estimate formula).

Figure 3:
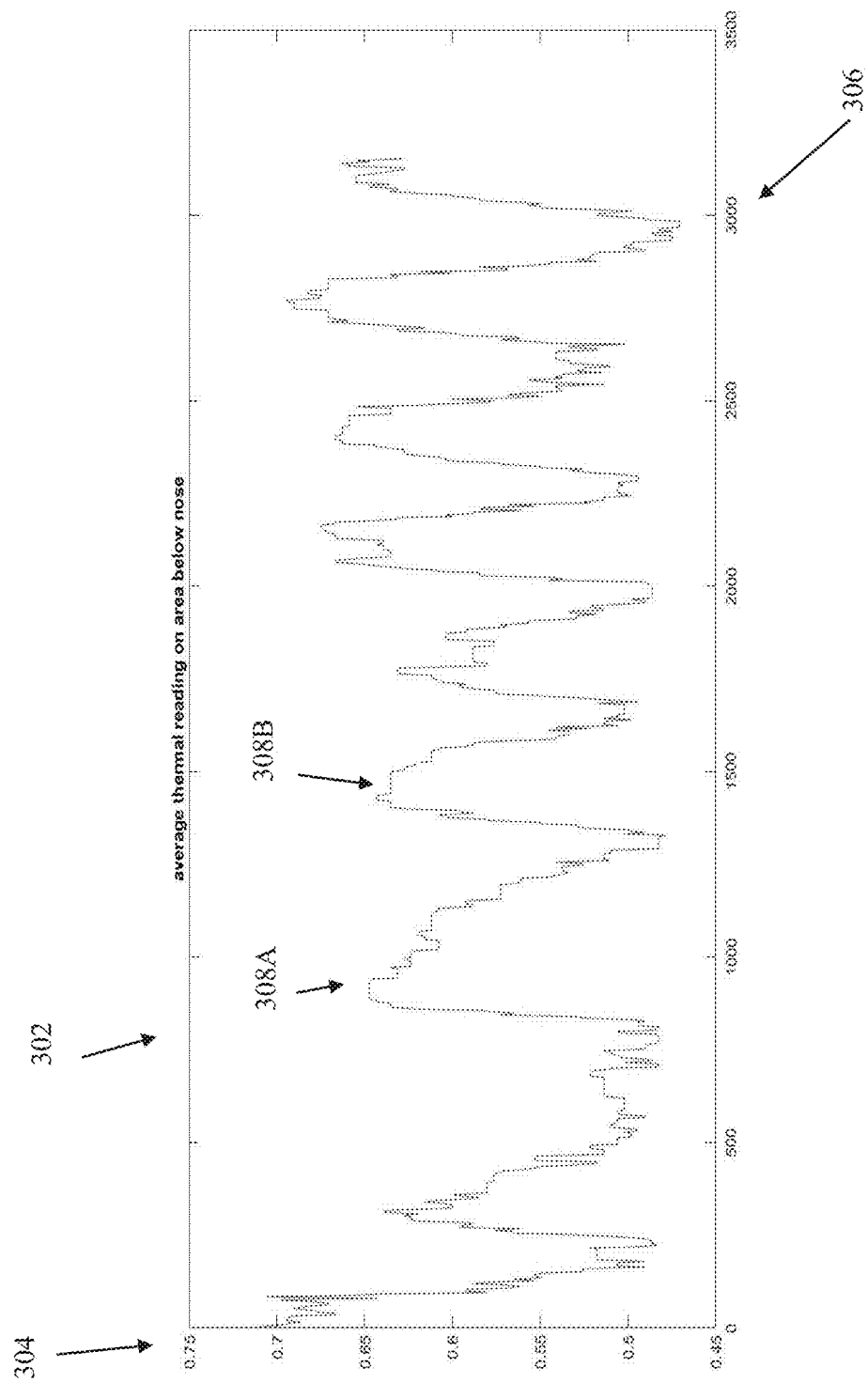
FIG. 3 is a graph for computation of sub-physiological parameter(s) generated from an analysis of multiple thermal images of a person, in accordance with some embodiments of the present invention.

Reference is now made to FIG. 3, which is a graph 302 for computation of sub-physiological parameter(s) generated from an analysis of multiple thermal images of a person, in accordance with some embodiments of the present invention. Y-axis 304 is a scale (e.g., normalized pixel intensity values) depicting a thermal reading indicative of temperature at an area below a nose of the person. It is noted that the temperature may be obtained at other locations described herein, for example, nostrils, inside a mouth cavity when the mouth is open, and regions of a mask being worn over the mouth and nose. X-axis 306 is an indication of time and/or sequence number of the images. Graph 302 is generated by plotting the respective temperature for the respective thermal image frame at the sequence number of the respective frame. The sub-physiological parameter, for example, respiratory rate may be computed, for example, based on local maximal temperature values, for example, a time between local maximal peak 308A and local maximal peak 308B indicates the time for one inspiratory/respiratory cycle. The respiratory rate may be obtained as the number of such inspiratory/respiratory cycles over one minute, or other measures.

Figure 4:
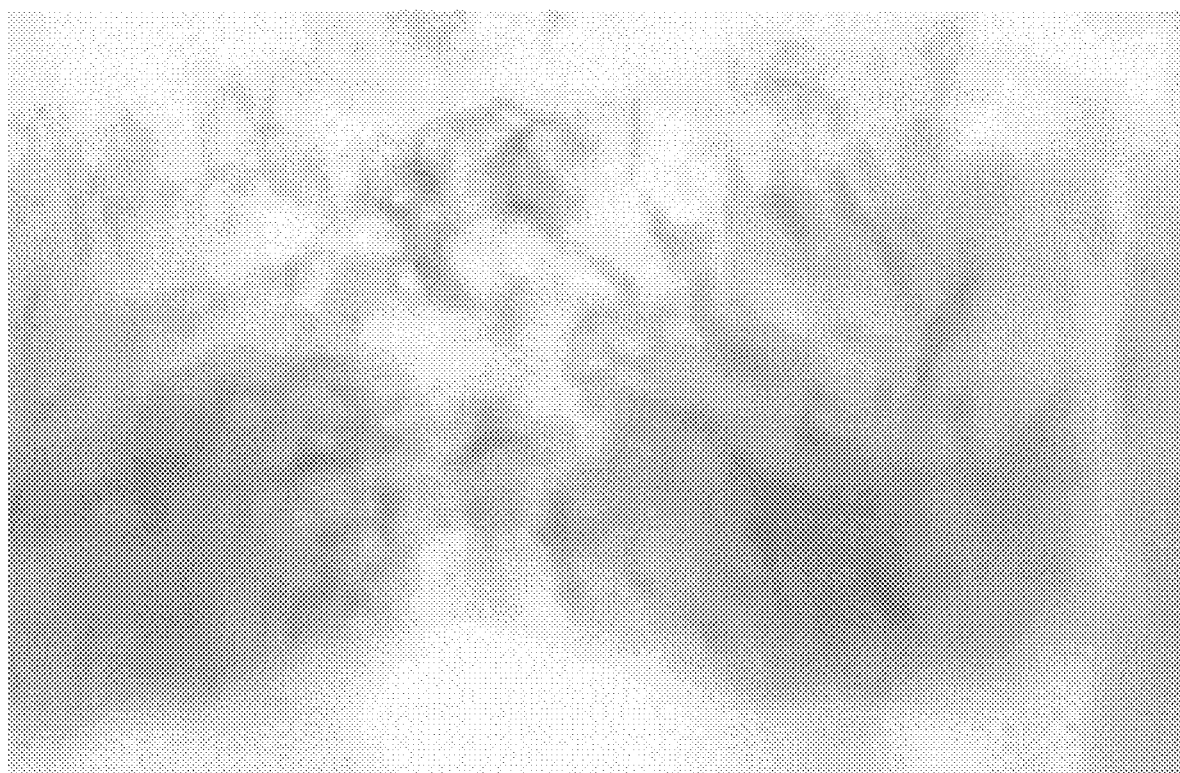
FIG. 4 is a thermal image of a chest used for computing sub-physiological parameter(s), in accordance with some embodiments of the present invention.

Reference is now made to FIG. 4, which includes an example of a thermal image 402 of a chest used to compute sub-physiological parameter(s), in accordance with some embodiments of the present invention. The thermal image may be obtained while the person is wearing the shirt (or other garment, or a blanket) or without the shirt. The thermal images of the chest may be analyzed to identify heating/cooling patterns. The sub-physiological parameter(s), for example, respiratory rate, may be computed based on the heating/cooling pattern, for example, by generating a graph of an indication of temperature as a function of frame sequence number (and/or time) as described with reference to FIG. 3, and/or other approaches described herein.

Figure 5:
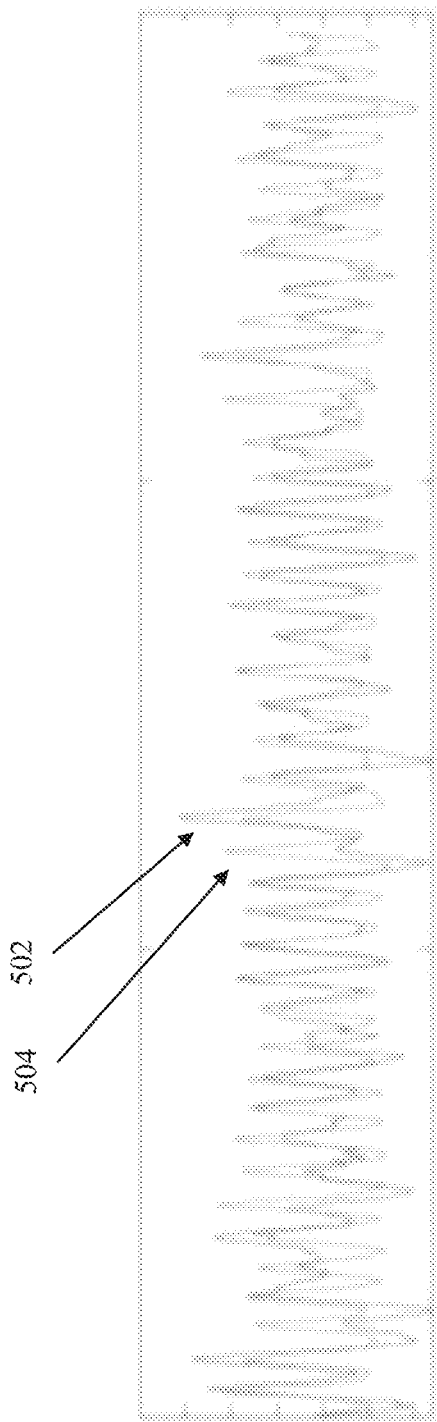
FIG. 5 is a graph created based on an output of a non-contact radar sensor sensing a chest of a person correlated with another graph created based on output of a contact belt sensor measuring the chest of the person, in accordance with some embodiments of the present invention.

Reference is now made to FIG. 5, which is an example of a graph 502 created based on an output of a non-contact radar sensor sensing a chest of a person correlated with another graph 504 created based on output of a contact belt sensor measuring the chest of the person, in accordance with some embodiments of the present invention. Graph 502 indicates that the non-contact sensor accurate generates an indication of movement of a chest (e.g., chest displacement) which may be used for computing sub-physiological parameter(s) such as respiratory rate and/or heart rate.

Figure 6:
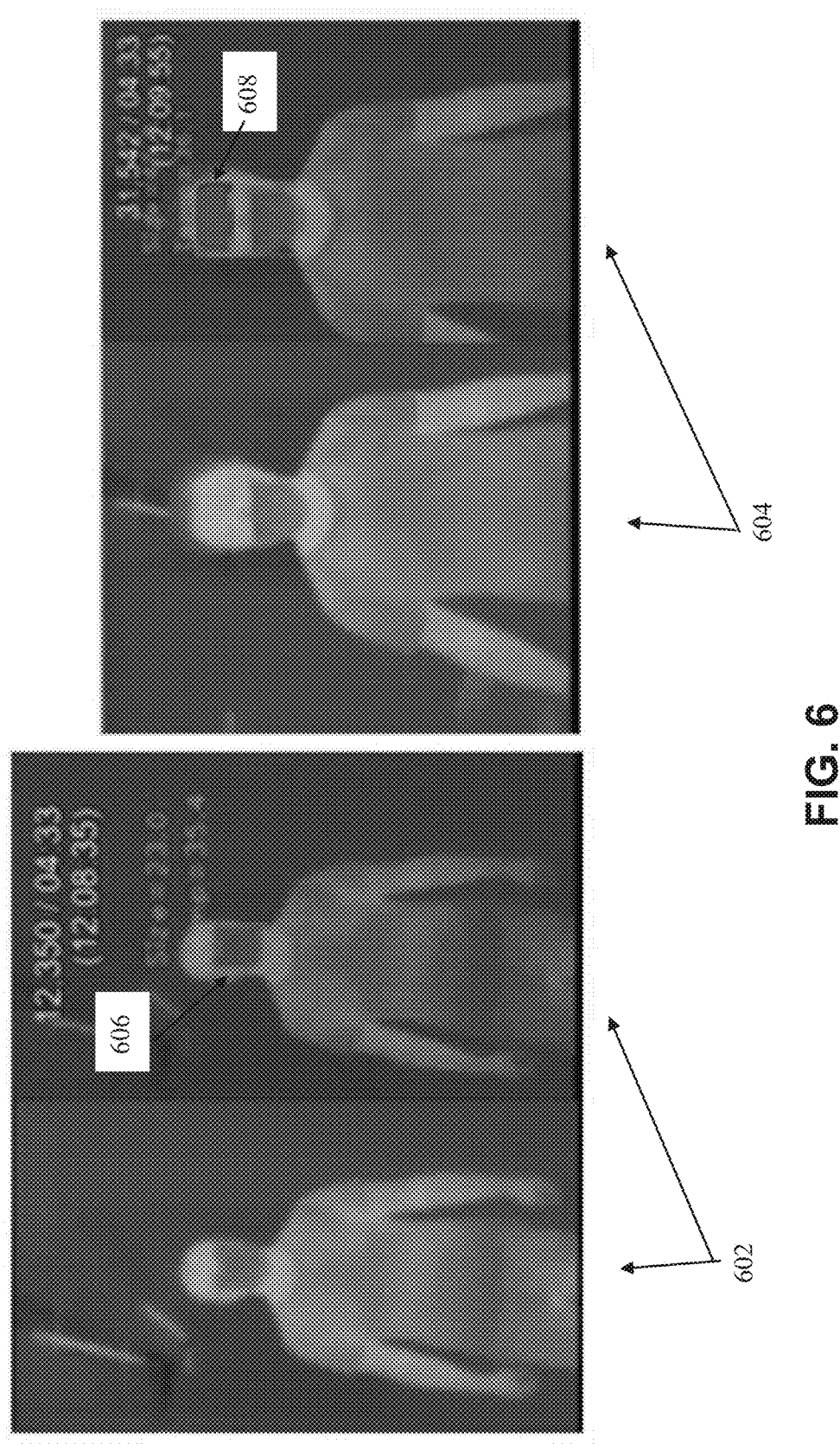
FIG. 6 includes thermal images that are analyzed to measure a temperature of an identified mask and/or measure a temperature of an identified forehead of the respective depicted person, in accordance with some embodiments of the present invention.

Reference is now made to FIG. 6, which includes thermal images 602 and 604 that are analyzed to measure a temperature of an identified mask 606 (measured at 35.4 degrees Celsius) and/or measure a temperature of an identified forehead 608 (measured at 36.1 degrees Celsius) of the respective depicted person, in accordance with some embodiments of the present invention. The mask and/or forehead may be segmented. Changes in the temperature of the mask may be analyzed to identify breathing patterns, as described herein.

Referring now back to 104 of FIG. 1, the thermal images may be analyzed to identify one or more facial features and/or mask features indicative of regions depicting parts of a face of the person, for example, when the person is depicted as wearing a mask, bulges of the mask created by the nose underneath may be detected.

One or more sub-physiological parameters (e.g., breathing pattern) may be computed by analyzing changes in pixel intensity values of pixels corresponding to nostrils and/or face mask and/or open mouth of the person according to the identified facial features and/or mask features. For example, when the person is not wearing a mask, the breathing pattern is computed based on changes in pixel intensity values of the pixels corresponding to the nostrils and/or open mouth. In another example, when the person is wearing a mask, the breathing pattern is computed based on changes in pixel intensity values of regions of the face mask.

The change in pixel intensity values varies by an amount corresponding to a temperature change range. A rate of change of the pixel intensity values corresponds to a candidate breathing rate range. The breathing pattern may be computed as a breathing rate based on a time interval from maximal to minimal (or maximal to maximal, or minimal to minimal, or minimal to maximal) pixel intensity values of pixels corresponding to the nostril and/or face mask of the sequence of thermal images. For example, certain regions of pixels of the mask of the person cycle between high and low pixel intensity values, indicating the breathing pattern of the person, breathing in cool air and exhaling warm air. The peak to peak time interval (e.g., peak pixel intensity time to another peak pixel intensity time) may represent the time between each exhalation. The time for each breath may be estimated as the minimal peak time indicating breathing in to maximal peak time indicating breathing out.

Figure 7:
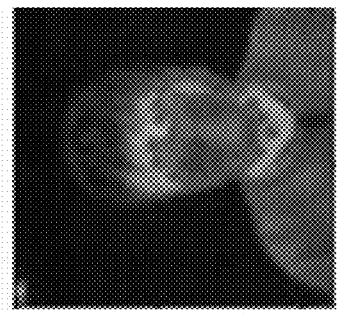
FIG. 7 includes thermal images depicting a person walking, for which facial features are identified, represented by stars, in accordance with some embodiments of the present invention.
Figure 7:
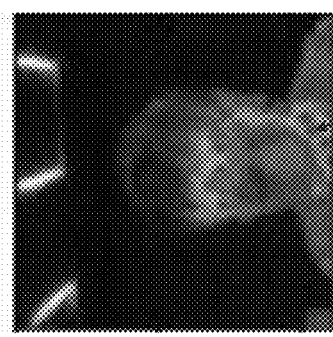
Figure 7:
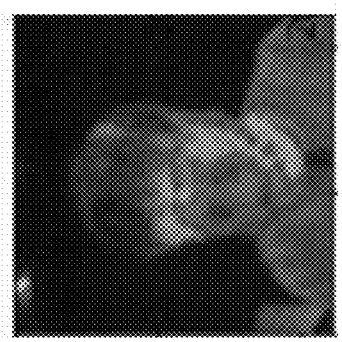
Figure 7:
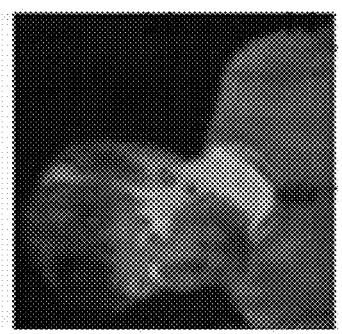
Figure 7:

Reference is now made to FIG. 7, which includes thermal images 702 depicting a person walking, for which facial features are identified, represented by stars 704, in accordance with some embodiments of the present invention. Sub-physiological parameters may be computed based on the detected facial features as described herein. Image 706 depicts one sample image, and a corresponding annotated image 708 with identified facial features. 710.

At 106, a combination of the sub-physiological parameters is analyzed. Alternatively or additionally, a combination of the datasets is analyzed.

Optionally, the combination of the sub-physiological parameters is analyzed according to the demographic parameter(s) of the person. The demographic parameter(s) may define a baseline from which other sub-physiological parameters may be determined to be normal or abnormal. For example, the breathing rate, heart rate, and/or temperature ranges considered as non-pathological (or pathological) for an obese 65 year old tall person are different than the breathing rate, heart rate, and/or temperature ranges for a short 15 year old, thin, short, athletic child. According to the first implementation, each sub-physiological parameter is different. Alternatively, according to the second implementation, each sub-physiological parameter is similar and/or the same.

The analysis of the combination of sub-physiological parameters and/or combination of datasets may be performed, for example, by applying a set of rules, computing a correlation between the datasets and/or the sub-physiological parameters, and/or inputting the combination of the sub-physiological parameters into a classifier trained on a dataset of combinations of sub-physiological parameters and a label of the physiological parameter indicative of physiological pathology.

As used herein, the term classifier may refer, for example, to a statistical classifier and/or machine learning model that maps inputs to an outcome. The classifier(s) described herein may be implemented, for example, to one or more neural networks of various architectures (e.g., artificial, deep, convolutional, fully connected), support vector machine (SVM), logistic regression, k-nearest neighbor, decision trees, and combinations of the aforementioned For example, according to the first implementation, likelihood of being infected with COVID-19 (or another viral illness) is determined based on a set of rules that evaluate multiple sub-physiological parameters computed from different datasets. For example, when temperature of a person's forehead obtained from a thermal image is above a first threshold, and a respiratory rate computed from a radar sensor measure chest motion of a chest of the person is above a second threshold, and an oxygen saturation level measured by an RGB and/or SWIR sensor is below a third threshold, likelihood of viral infection is detected.

For example, according to the second implementation, a value indicative of an amount of correlation between the datasets may be computed. For example, to compute respiratory rate, a graph of pixel intensity values of nostrils obtained from thermals images may be correlated with a graph of respiratory motion obtained from output of a radar sensor. At times when the two graphs have a correlation above a threshold, the respiratory rate may be computed from the correlated graphs (or from one of the two graphs during the time when the graphs are correlated).

At 108, the physiological parameter indicative of physiological pathology is computed according to the analysis. The physiological parameter may be, for example, likelihood of the subject being infected with the viral disease and/or likelihood of the subject suffering from physiological pathology. The physiological parameter may be represented, for example, as a value between 0-1 (or 0-100), a binary indication (e.g., yes/no), or one of multiple classification categories (e.g., none, mild, severe).

The physiological parameter may be computed, for example, by a mapping dataset that maps values of the sub-physiological parameters into the physiological parameter (e.g., in a multi-dimensional space), a function, and/or a classifier trained on a training dataset of sample datasets and/or combinations of sub-physiological parameters labelled with the physiological parameter. For example, the value of the physiological parameter is computed based on the values of the sub-physiological parameters, and/or number of rules met. For example, the higher the temperature, and the higher the respiratory rate, and the lower the oxygen saturation, the more likely that the person is infected with the viral illness.

In some embodiments, the extracting of the extracting of the sub-physiological parameters, and/or the analysis of the combination of the sub-physiological parameters, and/or the computing of the physiological parameter is performed by inputting the datasets based on the outputs of the different sensors into a classifier. The physiological parameter is obtained as an outcome of the classifier. The classifier is trained on a training dataset including, for each of multiple subjects, a respective dataset acquired by each of the remote non-contact sensors, and an associated label of the physiological parameter indicative of physiological pathology. In another example, the training dataset includes, for each of multiple subjects, the combination of sub-physiological parameters and the associated label of the physiological parameter.

At 110, instructions may be automatically generated according to the physiological parameter. The instructions may be, for example, code and/or other signals for execution by a controller. The controller may be, for example, for automatic opening and/or closing of a door for entry to an enclosure such as an office building, subway, airport, mall, and a movie theater. The door may be instructed to open for admission to the person when the physiological parameter indicates unlikelihood of physiological pathology, for example, unlikely to be infected with the viral disease. The door may be instructed to close and/or to maintain the door in the closed state to prevent admission of the person when the physiological parameter indicates likelihood of physiological pathology, for example, when the person is likely infected with the viral disease.

In another example, the subject may be sitting in a vehicle (e.g., car). The datasets (e.g., as in 102) depict the subject in the vehicle captured with a window of the vehicle open. In another example, where the car window is closed, the analysis may be performed for closed windows, for example, training classifiers on datasets of subjects in cars with closed windows. Instructions are generated for admitting the vehicle to a parking area and/or to let the vehicle keep on driving when the physiological parameter is below a threshold, optionally automatically activating a mechanism to open a gate and/or generating an indication for a user to manually open the gate. When the physiological parameter is above the threshold, the gate may remain closed, denying the vehicle admission.

In other examples, the instructions may be, for example, to trigger an alert to a user. For example, when a person with the viral disease is in home isolation and being remotely monitored for respiratory difficulties due to the viral disease. The alert may be generated, for example, as a text message, a phone call, an email, and/or a pop-up message on a mobile device and/or administrative server of the user, warning that the condition of the person being monitored is becoming more severe.

At 112, an effective treatment may be administered for treatment of the physiological pathology and/or the person may be sent for additional testing. For example, when the physiological pathology is COVID-19 and/or shortness of breath, a treatment effective for COVID-19 and/or shortness of breath is administered, for example, supplemental oxygen, antibiotics, anti-viral, mechanical ventilation, bronchodilators, and corticosteroids. In another example, the person may be sent for additional testing, for example, x-ray, ECG, CT scan, pulmonary examination, and the like.

Optionally, at 114, prior to extraction of the sub-physiological parameter as in 104, a first dataset captured by a first sensor is analyzed for calibrating and/or directing the second sensor for the simultaneous capture of the second dataset, as described with reference to 102.

In an example, the first remote non-contact sensor is a thermal and/or visual sensor that captures a sequence of thermal and/or visual images depicting a chest and/or head of the person. The second remote non-contact sensors is a Doppler and/or radar sensor. One or more thermal and/or visual images are analyzed to identify a target location of the chest and/or head of the person depicted therein.

At 116, based on the analysis of the first dataset, the second sensor is calibrated. The values of the first dataset are used to adjust the second sensor to obtain an improved second dataset. The combination of the first and second datasets may improve the accuracy of the physiological parameter.

Optionally, instructions are generated for automatic adjustment of a steering mechanism for adjusting an orientation of the second sensor (e.g., Doppler and/or radar sensor) for capturing the second dataset according to the target location identified in the first dataset (i.e., the thermal images).

At 118, one or more of 102-112 are implemented. At 102, the first and second datasets are then simultaneously received from the first sensor and the calibrated and/or directed second sensor. At 104, a first sub-physiological parameter is extracted from the first dataset acquired by the first sensor (e.g., thermal and/or visual sensor), and a second sub-physiological parameter is extracted from the second dataset acquired by the second sensor (e.g., Doppler and/or radar sensor).

At 120, during (e.g., before, after, during, simultaneously with) 102, a certain dataset acquired by a certain remote non-contact sensor is analyzed to obtain tracked locations on multiple fixed points on the head of the person. The certain sensor may be a camera (e.g., thermal, visual) that generates thermal and/or visual images. The images are analyzed to obtain the tracked locations.

At 122, an additional dataset depicting the head of the person acquired by another remote non-contact sensor, which is different than the certain sensor, is received. The additional dataset is corrected using the fixed points of the certain dataset, for tracking the fixed points on the head of the person depicted in the additional dataset.

At 124, one or more of 104-112 are implemented using the corrected additional dataset.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant sensors will be developed and the scope of the term sensor is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A system for measuring a physiological parameter of a person indicative of physiological pathology, comprising:
a plurality of remote non-contact sensors, each of a different type of sensing modality,
wherein each one of the plurality of remote non-contact sensors is in non-physical contact with a person being monitored and is spaced apart from the person being monitored;
at least one hardware processor executing a code for:
simultaneously receiving over a time interval, from each of the plurality of remote non-contact sensors monitoring a person, a respective dataset,
wherein the respective dataset is obtained remotely without the respective remote non-contact sensor physically contracting the person;
extracting, from each respective dataset, a respective sub-physiological parameter of a plurality of sub-physiological parameters;
analyzing a combination of the plurality of sub-physiological parameters; and
computing a physiological parameter indicative of physiological pathology according to the analysis,
wherein an accuracy of the physiological parameter computed from the combination is higher than an accuracy of the physiological parameter independently computed using any one of the plurality of sub-physiological parameters;
wherein prior to the extracting:
detecting errors according to an analysis of a combination of the datasets when time synchronized;
correcting and/or removing the detected errors from the datasets,
wherein the extracting is performed for each respective dataset for which the detected errors are corrected and/or removed.

2. A system for measuring a physiological parameter of a person indicative of physiological pathology, comprising:
a plurality of remote non-contact sensors, each of a different type of sensing modality,
wherein each one of the plurality of remote non-contact sensors is in non-physical contact with a person being monitored and is spaced apart from the person being monitored;
at least one hardware processor executing a code for:
simultaneously receiving over a time interval, from each of the plurality of remote non-contact sensors monitoring a person, a respective dataset,
wherein the respective dataset is obtained remotely without the respective remote non-contact sensor physically contracting the person;
extracting, from each respective dataset, a respective sub-physiological parameter of a plurality of sub-physiological parameters;
analyzing a combination of the plurality of sub-physiological parameters; and
computing a physiological parameter indicative of physiological pathology according to the analysis,
wherein an accuracy of the physiological parameter computed from the combination is higher than an accuracy of the physiological parameter independently computed using any one of the plurality of sub-physiological parameters;
wherein a first of the plurality of remote non-contact sensors comprises a thermal and/or visual sensor capturing a sequence of thermal and/or visual images depicting a chest and/or head of the person, a second of the plurality of remote non-contact sensors comprises a Doppler and/or radar sensor, and further comprising code for:
analyzing at least one thermal and/or visual image to identify a target location of the chest and/or head of the person; and
generating instructions for adjustment of a steering mechanism for adjusting an orientation of the Doppler and/or radar sensor for capturing the dataset from the identified target location,
wherein a first sub-physiological parameter is extracted from a first dataset acquired by the thermal and/or visual sensor, and a second sub-physiological parameter is extracted from a second dataset acquired by the Doppler and/or radar sensor.

3. A system for measuring a physiological parameter of a person indicative of physiological pathology, comprising:
a plurality of remote non-contact sensors, each of a different type of sensing modality,
wherein each one of the plurality of remote non-contact sensors is in non-physical contact with a person being monitored and is spaced apart from the person being monitored;
at least one hardware processor executing a code for:
simultaneously receiving over a time interval, from each of the plurality of remote non-contact sensors monitoring a person, a respective dataset,
wherein the respective dataset is obtained remotely without the respective remote non-contact sensor physically contracting the person;
extracting, from each respective dataset, a respective sub-physiological parameter of a plurality of sub-physiological parameters;
analyzing a combination of the plurality of sub-physiological parameters; and
computing a physiological parameter indicative of physiological pathology according to the analysis,
wherein an accuracy of the physiological parameter computed from the combination is higher than an accuracy of the physiological parameter independently computed using any one of the plurality of sub-physiological parameters;
analyzing a first dataset acquired by a first remote non-contact sensor to obtain tracked locations on a plurality of fixed points on a head of the person;
receiving a second dataset depicting the head of the person acquired by a second remote non-contact sensor; and
correcting the second dataset using the fixed points of the first dataset, for tracking the plurality of fixed points on the head of the person depicted in the second dataset.

4. The system of claim 1, wherein the plurality of sub-physiological parameters and corresponding remote non-contract sensors are selected from the group consisting of:
(i) temperature computed from an analysis of a thermal images captured by a thermal sensor;
(ii) respiratory rate and/or breathing pattern computed from an analysis of data outputted by a sensor selected from the group consisting of: a thermal sensor, a radar sensor, a Doppler sensor, and a short wave infrared sensor (SWIR) sensor;
(iii) heart rate and/or heartbeat pattern computed from an analysis of data outputted by a sensor selected from the group consisting of: a radar sensor, a Doppler sensor, a thermal sensor, and a visual light sensor;
(iv) oxygen saturation (SpO2) computed from an analysis of data outputted by a sensor selected from the group consisting of: a SWIR sensor, and a visual light sensor;
(v) one or more of: nasal congestion, sore throat, hoarse voice, and cough, obtained from an analysis of an acoustic dataset outputted by an acoustic sensor.

5. The system of claim 1, wherein each sub-physiological parameter denotes a measurement of a different physiological manifestation of the person, and the physiological parameter indicates a diagnosis of likelihood of physiological pathology,
wherein none of the sub-physiological parameters when used independently are indicative of the diagnosis of likelihood of physiological pathology.

6. The system of claim 5, further comprising at least one of:
(i) automatically generating instructions to a controller that controls an automatic door to open the door for admission of the person when the diagnosis indicates unlikelihood of physiological pathology, and to close the door and/or maintain the door in the closed state to prevent admission of the person when the diagnosis indicates likelihood of physiological pathology, and
(ii) administering an effective treatment for treatment of the physiological pathology, the treatment selected from the group consisting of: supplemental oxygen, antibiotics, anti-viral, mechanical ventilation, bronchodilators, and corticosteroids.

7. A system for measuring a physiological parameter of a person indicative of physiological pathology, comprising:
a plurality of remote non-contact sensors, each of a different type of sensing modality,
wherein each one of the plurality of remote non-contact sensors is in non-physical contact with a person being monitored and is spaced apart from the person being monitored;
at least one hardware processor executing a code for:
simultaneously receiving over a time interval, from each of the plurality of remote non-contact sensors monitoring a person, a respective dataset,
wherein the respective dataset is obtained remotely without the respective remote non-contact sensor physically contracting the person;
extracting, from each respective dataset, a respective sub-physiological parameter of a plurality of sub-physiological parameters;
analyzing a combination of the plurality of sub-physiological parameters; and
computing a physiological parameter indicative of physiological pathology according to the analysis,
wherein an accuracy of the physiological parameter computed from the combination is higher than an accuracy of the physiological parameter independently computed using any one of the plurality of sub-physiological parameters;
wherein the subject is in a vehicle, and the respective datasets depict the subject in the vehicle captured with a window of the vehicle open.

8. The system of claim 7, further comprising code for generating instructions for admitting the vehicle to a parking area when a value of the physiological pathology is below a threshold.

9. A system for measuring a physiological parameter of a person indicative of physiological pathology, comprising:
a plurality of remote non-contact sensors, each of a different type of sensing modality,
wherein each one of the plurality of remote non-contact sensors is in non-physical contact with a person being monitored and is spaced apart from the person being monitored;
at least one hardware processor executing a code for:
simultaneously receiving over a time interval, from each of the plurality of remote non-contact sensors monitoring a person, a respective dataset,
wherein the respective dataset is obtained remotely without the respective remote non-contact sensor physically contracting the person;
extracting, from each respective dataset, a respective sub-physiological parameter of a plurality of sub-physiological parameters;
analyzing a combination of the plurality of sub-physiological parameters; and
computing a physiological parameter indicative of physiological pathology according to the analysis,
wherein an accuracy of the physiological parameter computed from the combination is higher than an accuracy of the physiological parameter independently computed using any one of the plurality of sub-physiological parameters;
analyzing at least one of the respective datasets obtained from at least one of the plurality of remote non-contact sensors for validating that a set of rules is met, and in response to the set of rules being met, performing the extracting, the analyzing the combination, and the computing the physiological parameter, wherein the set of rules includes at least one rule selected from a group consisting of: a subject is in a vehicle, a window of the vehicle is open, a location of the subject and/or vehicle is according to a target location, an engine of the vehicle is turned off, and vibrations of the vehicle are below a threshold.

10. A system for measuring a physiological parameter of a person indicative of physiological pathology, comprising:
a plurality of remote non-contact sensors, each of a different type of sensing modality;
at least one hardware processor executing a code for:
simultaneously receiving over a time interval, from each of the plurality of remote non-contact sensors monitoring a person, a respective dataset;
extracting, from each respective dataset, a respective sub-physiological parameter of a plurality of sub-physiological parameters;
analyzing a combination of the plurality of sub-physiological parameters; and
computing a physiological parameter indicative of physiological pathology according to the analysis,
wherein each respective sub-physiological parameter denotes a different respective measurement originating from a same single physiological manifestation of the person, and the physiological parameter indicative of physiological pathology is a single measurement of the same single physiological manifestation,
wherein an accuracy of the physiological parameter computed from the combination is higher than an accuracy of the physiological parameter independently computed using any one of the plurality of sub-physiological parameters;

wherein a time interval of the datasets used for computing the physiological parameter is shorter than a time interval of each respective dataset required to compute each respective sub-parameter with an accuracy similar to an accuracy of the physiological parameter.

11. The system of claim 10, wherein the same single physiological manifestation indicative of physiological pathology is selected from the group consisting of: (i) respiratory rate and/or breathing pattern, (ii) heart rate and/or heartbeat pattern, and (iii) blood oxygen saturation (SpO2), and wherein the datasets and corresponding remote non-contract sensors include two or more sensors selected from the group consisting of: (i) thermal images acquired by a thermal sensor, (ii) near infrared (NIR) images acquired by a NIR sensor, (iii) visual light images acquired by a visual light sensor, and a (iv) dataset indicative of chest motion captured by a Doppler sensor and/or radar sensor.

12. A system for measuring a physiological parameter of a person indicative of physiological pathology, comprising:
a plurality of remote non-contact sensors, each of a different type of sensing modality,
wherein at least one of the plurality of remote non-contact sensors comprise a thermal sensor capturing a sequence of thermal images depicting an open mouth of a person;
at least one hardware processor executing a code for:
simultaneously receiving over a time interval, from each of the plurality of remote non-contact sensors monitoring the person, a respective dataset;
extracting, from each respective dataset, a respective sub-physiological parameter of a plurality of sub-physiological parameters,
wherein at least one of the plurality of sub-physiological parameters comprise a breathing pattern;
computing the breathing pattern by analyzing changes in pixel intensity values of at least one of:
(i) pixels corresponding to a mouth cavity of the person in the sequence of thermal images, and (ii) pixels corresponding to nostrils and/or face mask of the person in the sequence of thermal images;
analyzing a combination of the plurality of sub-physiological parameters; and
computing a physiological parameter indicative of physiological pathology according to the analysis,
wherein an accuracy of the physiological parameter computed from the combination is higher than an accuracy of the physiological parameter independently computed using any one of the plurality of sub-physiological parameters.

13. The system of claim 12, further comprising code for segmenting the nostrils and/or mask of the person in the sequence of thermal images by identifying regions of changes in pixel intensity values, the change in pixel intensity values varies by an amount corresponding to a temperature change range, and a rate of change of the pixel intensity values corresponding to a candidate breathing rate range.

14. The system of claim 12, wherein the breathing pattern is computed as a breathing rate based on a time interval from maximal to maximal pixel intensity values of pixels corresponding to the nostril and/or face mask of the sequence of thermal images.

15. The system of claim 12, wherein analyzing changes in pixel intensity values comprises analyzing an average intensity value of intensity values of pixels depicting the face mask and/or nostrils.

16. The system of claim 12, wherein the change in pixel intensity values of pixels corresponding to the face mask excludes pixels of the face mask corresponding to a nose of the person.

17. The system of claim 12, wherein the breathing pattern is computed by analyzing changes in pixel intensity values of pixels corresponding to a region on a face of the person under a nose of the person in the sequence of thermal images.

18. The system of claim 12, further comprising code for analyzing the sequence of thermal images to identify a plurality of facial features and/or mask features indicative of regions of each thermal image depicting parts of a face of the person, wherein the breathing pattern is computed by analyzing changes in pixel intensity values of pixels corresponding to nostrils and/or face mask of the person according to the identified plurality of facial features and/or mask features.

* * * * *